March 12, 1963 G. J. VON ABRAMS Plant Pat. 2,242
ROSE PLANT
Filed May 11, 1962 2 Sheets-Sheet 1
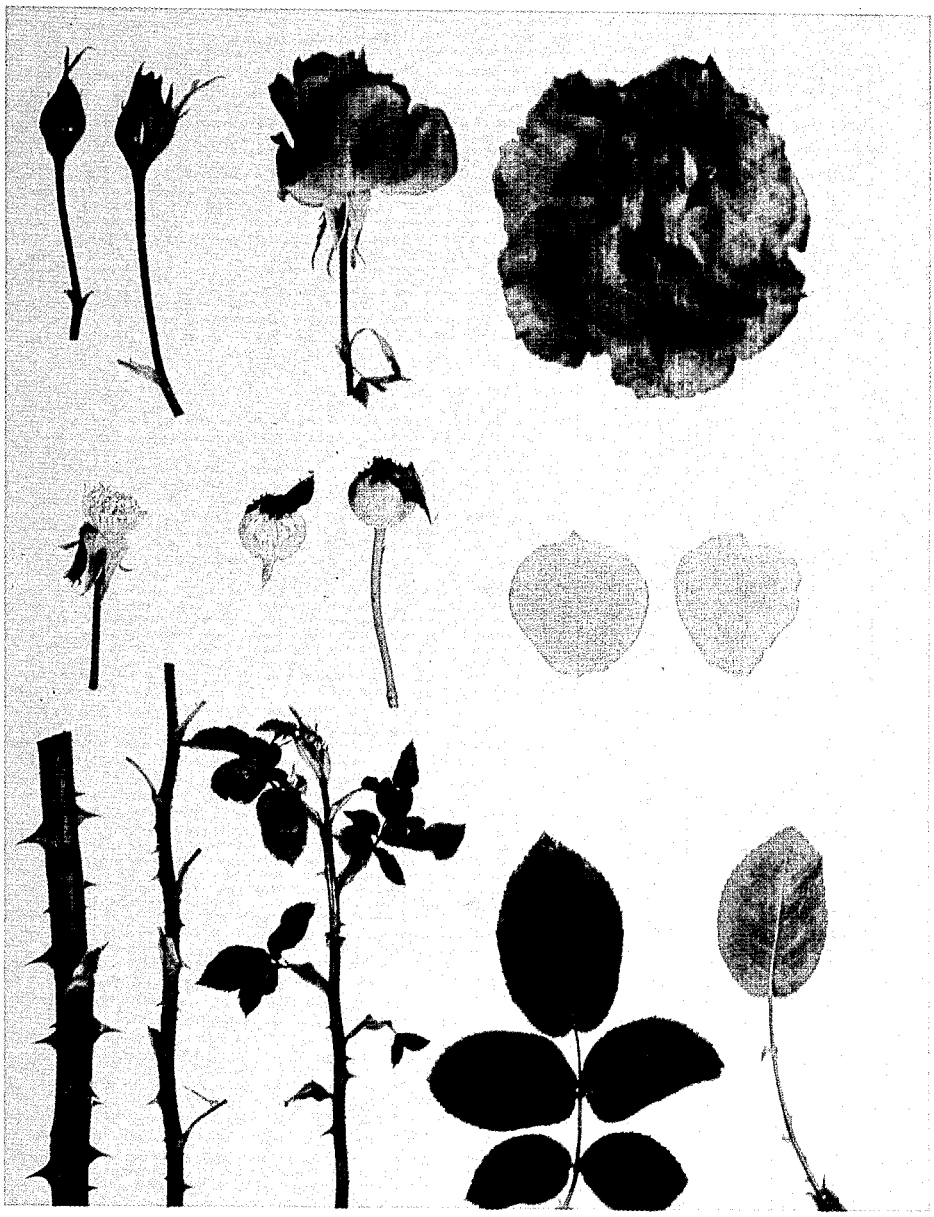
Inventor:
Gordon J. Von Abrams March 12, 1963 G. J. VON ABRAMS Plant Pat. 2,242
ROSE PLANT
Filed May 11, 1962 2 Sheets-Sheet 2
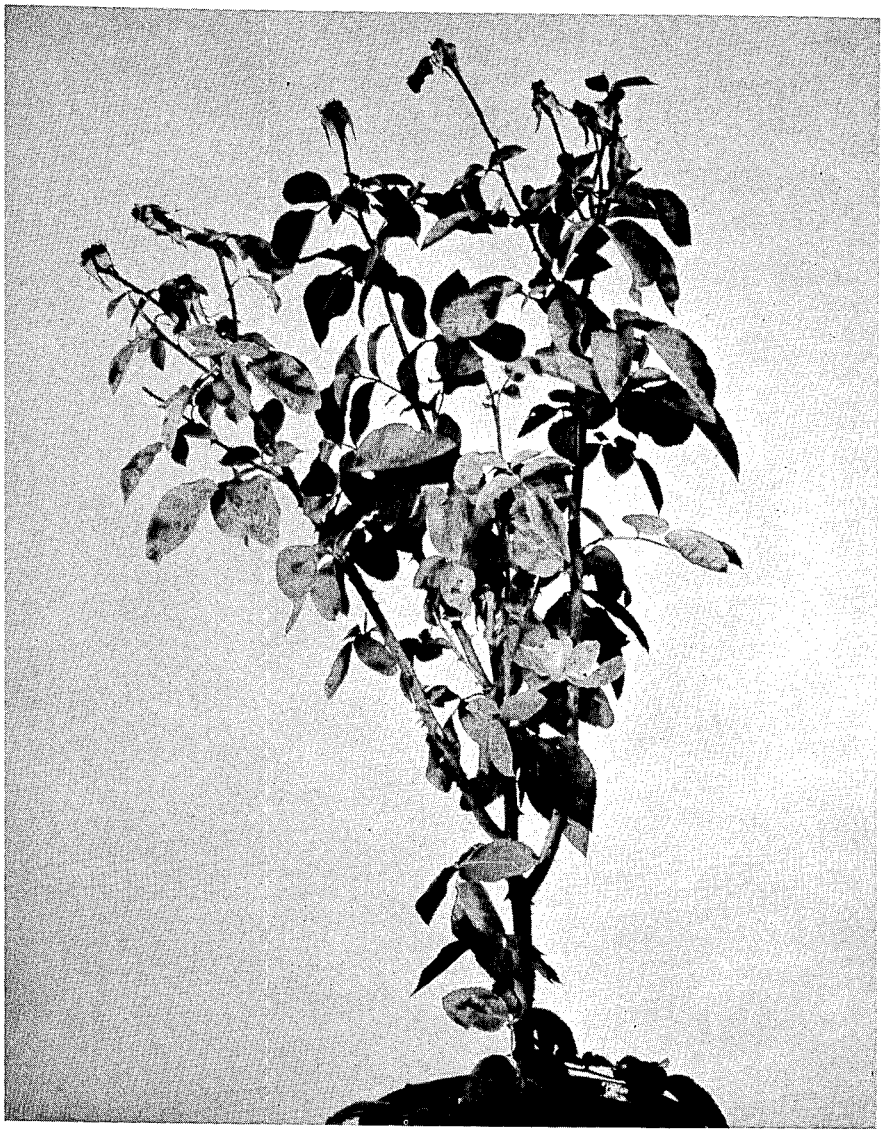
Inventor
Gordon J. VonAbrams United States Patent Office Plant Pat. 2,242
Patented Mar. 12, 1963

2,242
ROSE PLANT
Gordon J. Von Abrams, 3463 NW. Savier St., Portland, Oreg.
Filed May 11, 1962, Ser. No. 194,207
1 Claim. (Cl. 47—61)

The present invention constitutes a new and distinct variety of rose plant of the commercial "grandiflora" class, originated by me by cross-pollinating the variety Carrousel (Plant Patent No. 1,066) with the variety PD No. 5361–A (previously originated by me, not patented and not in commerce).

The following objectives, for which this breeding was planned and executed, were achieved:

(1) Tall, very vigorous plant habit;
(2) Exceptional floriferousness;
(3) Very bright red flower color; and
(4) Flowers borne on long secondary stems, some borne singly, but most borne in clusters of several to many on each main stem.

The symmetry of flower form in relation to the regularly ruffled petals, in addition to the flower color, type of inflorescence and general plant habit, and in addition to the particular complement of other phenotypic characteristics, makes this new variety worthy and distinct from other varieties currently in commerce or otherwise known to me.

The new variety differs from its seed parent, "Carrousel," in the following respects:

The flower color of the new variety is somewhat brighter, not as dark, as that of "Carrousel";

The petals are more numerous, more ruffled but more regular in outline, more symmetrically arranged, and the inside petals of the opening flower are less cupped;

The stamens are fewer in number;

The leaf is slightly less accuminate; and

The thorns are generally more numerous than on "Carrousel."

The new variety shows little phenotypic resemblance to its pollen parent, "PD No. 6361–A," differing most obviously in having a taller and more upright plant habit, fewer petals, brighter flower color, more regular flower form, and less disease resistance than the pollen parent.

The pollination from which this new variety resulted was performed by me in 1954. The variety was first asexually reproduced in 1956 by bud-grafting, and has retained its distinguishing characteristics through the succession of such vegetative propagations since that time.

The accompanying illustrations were made in September 1961, of specimens grown outdoors at Scappoose, Oregon. The illustration in color shows vegetative and reproductive parts of the new variety in various stages of development. The black-and-white illustration shows a typical inflorescence of the new variety.

The following detailed description of the new variety was prepared in August 1961, from specimens propagated and grown outdoors at Scappoose, Oregon. To the best of my ability, colors, wherever pertinent, have been defined with reference to the following color standards:

(1) Ridgway, R.; Color Standards and Color Nomenclature, Washington, D.C., 1912.
(2) Wilson, R. F.; Royal Horticultural Society Colour Chart, England, 1940.

*Reproductive Parts*

Quantity of bloom: Very abundant.

Continuity of bloom: Nearly continuous during growing season.

Inflorescence: Flowers borne sometimes one, but more often several to many per main stem; on moderately strong, medium to long secondary stems.

Flower bud:

*Pedicel.*—Medium caliber; long to very long (i.e.—from 6 to 10 cm.); erect; color near Scheele's Green (Ridgway, 33. GY-G. *i*, Plate VI), variably flushed maroon; surface with numerous reddish gland-tipped cilia.

*Sepals.*—Size—medium large (i.e.—1 x 3.2 cm.). Form—spear shape. Point—medium size; aristate; sometimes foliaceous, rarely very foliaceous. Lateral margins—glandular cilia few or none; most with 2 to 3 bristle-like appendages. Surface: outer—somewhat rough; slightly glaucous; not ciliate; inner — moderately tomentose. Color: outer surface—near Courge Green (Ridgway, 25′. YG-Y. *i*, Plate XVII), variably flushed maroon; inner surface—near Kildare Green (Ridgway, 29″. GG-Y. *b*, Plate XXXI). Behavior—reflex.

*Before calyx breaks.*—Size—medium. Form—medium tapered point; terminal appendages usually medium aristate or rarely long foliaceous.

*As calyx breaks.*—Exposed petal color near Purple Madder (Wilson, 1028, p. 181) or darker, to near black.

*As first petal opens.*—Petal color: outer surface—darker and somewhat bluer than Cardinal Red (Wilson, 822, p. 168) irregularly flushed darker, to near black; small yellow mark at base. Inner surface—dark intense velvety crimson, related to, but clearer and deeper than Cardinal Red (Wilson, 822, p. 168); bright yellow mark at base, near Canary yellow (Wilson, 2, p. 2).

*Opening habit.*—Opens gracefully.

Open flower:

*Size.*—Medium (i.e.—10. cm.).

*Petalage.*—Double, i.e.—24 to 35 petals.

*Form.*—Reflexed, with center open but not depressed in profile. Petal distribution regular and symmetrical. Petals somewhat ruffled, that is, undulant or wave-form in apical transverse section.

*Fragrance.*—Faint.

Petals:

*Substance.*—Medium thick; firm; flexible.

*Texture.*—Outside shiny; inside velvety.

*Shape and size in open flower.*—Petals generally ruffled, as described above. Outside petal—broadly obovate (i.e.—5 cm. broad by 4.5 cm. long); apex rounded but irregular. Intermediate petal—obovate (i.e.—4 cm. broad by 4.5 cm. long); apex rounded or irregularly notched. Inside petal—generally obovate, but smaller and somewhat irregular or contoured.

Flower color:

*Newly opened flower (August 1961, outdoors).*—Outside petal: outer (dorsal) surface—related to Cardinal Red (Wilson, 822/2, p. 168), but somewhat darker and slightly bluer, small basal fan near Canary Yellow (Wilson, 2, p. 2); inner (ventral) surface—related to Cherry (Wilson, 722, p. 157), but darker and more intense; basal fan near Canary Yellow (Wilson, 2, p. 2). Intermediate petal: outer (dorsal) surface—lighter than outside petal; somewhat bluer and darker than Cherry (Wilson, 722/2, p. 157); small yellow mark at base; inner (ventral) surface—lighter than outside petal; slightly darker than Cherry (Wilson, 722, p. 157), and more intense; yellow mark at base. Inside petal—as intermediate petal. General color effect—related to Cherry (Wilson, 722, p. 157), but darker and more intense.

*Flower three days after opening (August 1961, outdoors).*—Outside petal: outer (dorsal) surface—darker and grayer than Rose Red (Wilson, 724, p.

158); somewhat paler toward base, near Rose Red (Wilson, 724/3, p. 158); small pale yellow mark at base; inner (ventral) surface—related to Rose Red (Wilson, 724, p. 158), but slightly less blue, and much deeper and more intense; paler, near (Wilson, 724/1, p. 158) toward base; apical margin sometimes near-black; pale yellow mark at base. Intermediate petal: outer (dorsal) surface—grayer than Rose Red (Wilson 724/1, p. 158); pale yellow mark at base; inner (ventral) surface—near Rose Red (Wilson, 724/1, p. 158); apical ⅓ to ½ much deeper and more intense, usually stippled with small very dark to near black markings; small mark at base near Straw Yellow (Wilson 604, p. 67). Inside petal—as intermediate petal, except that the inner (ventral) surface shows less paling toward the base. General color effect—darker and deeper than Rose Red (Wilson, 724, p. 158).

Behavior in senescence: General bluing and fading, particularly near center. Petals drop cleanly. Outer edges may become near-black, with a burned appearance, in hot weather.

Longevity of flower: Ordinary.

Stamens: Quantity moderate. Filaments medium length (i.e.—8 mm.). Anthers small. Pollen moderately abundant; mostly viable.

Pistils: Quantity moderate. Styles free, little contorted, medium size. Stigmas ordinary. Ovaries enclosed.

Receptacle and calyx tube: Small, nearly conical. Disc low, rounded, not conspicuous. Surface glaucous. Color near Malachite Green (Ridgway, 35″. GREEN *b*, Plate XXXII).

Seed pod (fruit aggregate): Quantity moderate. Size medium; shape globose. Sepals generally persist. Surface glossy; wall thick and fleshy. Color—bright orange, variable.

Seeds: Ordinary; medium size; viability moderate.

*Vegetative Parts*

Foliage:

*Leaves.*—Compound, usually 5 leaflets; abundant; medium size.

*Leaflets.*—Substance—thick; medium hard; flexible. Texture — smooth; semi-glossy. Size — medium (i.e.—terminal leaflet 4.3 x 6.5 cm. to 6 x 9.5 cm.).

Shape—ovate; base rounded, sometimes slightly cordate; apex slightly acuminate; margin serrate. Color: mature—upper surface—darker than Spinach Green (Wilson, 0960, p. 187); lower surface—near Light Hellebore Green (Ridgway, 25′. YG-Y. *k*, Plate XVII); young—upper surface—near Maroon (Ridgway, 3. O-R. *m*, Plate I) variably flushed green; lower surface—near Victoria Lake (Ridgway, 1. RED *m*, Plate I), or somewhat lighter.

*Rachis.*—Caliber medium. Upper side—groove somewhat reduced; lateral ridges with few glandular cilia. Under side—small thorns few or none.

*Stipules.*—Size—small-medium (i.e.—6 x 13 mm. to 6 x 20 mm.). Points—medium; mostly straight, angle near 45°. Margins glandular.

*Disease resistance.*—Ordinary.

Plant body:

*Habit of growth.*—Tall, bushy, upright.

*Vigor.*—Strong.

*Canes (in second year of growth).*—Caliber—medium large. Surface—quite corky; several medium to small grayish thorns. Color greenish gray.

*Main stems (of current year's growth).*—Caliber—medium. Surface—moderately smooth, with some corkiness. Several medium small grayish thorns. Color grayish green.

*Branches (currently bearing fruit).*—Caliber—medium. Surface—smooth; thorns—several medium sized; tan to reddish-brown; hooked moderately downward. Color—grayish green; often strongly flushed unilaterally near maroon.

*New shoots.*—Surface—smooth, glacous; thorns—several medium, several small; color maroon; few gland-tipped cilia. Color—light grayish green, heavily to near entirely flushed maroon.

I claim:

A new and distinct variety of rose plant, of the commercial "grandiflora" class, substantially as shown and described, characterized particularly by the form of the flower, by the bright red flower color, by the floriferousness and type of inflorescence, and by the tall vigorous plant habit, all as disclosed herein.

No references cited.